US00PP20020P2

(12) United States Plant Patent
Wood

(10) Patent No.: US PP20,020 P2
(45) Date of Patent: May 26, 2009

(54) ***HYDRANGEA* PLANT NAMED 'ROBERT'**

(50) Latin Name: *Hydrangea macrophylla*
Varietal Denomination: Robert

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/075,449

(22) Filed: Mar. 11, 2008

(51) Int. Cl.
*A01H 5/00* (2006.01)

(52) U.S. Cl. ..... Plt./250
(58) Field of Classification Search ..... Plt./250
See application file for complete search history.

*Primary Examiner*—S. B McCormick Ewoldt
(74) *Attorney, Agent, or Firm*—C. A. Whealy

(57) ABSTRACT

A new and distinct cultivar of *Hydrangea* plant named 'Robert', characterized by its upright and mounded plant habit; strong roots and stems; strong and dark green-colored leaves; and large mophead-type inflorescences with dark pink-colored flowers.

1 Drawing Sheet

Botanical designation: *Hydrangea macrophylla.*
Cultivar denomination: 'Robert'.

BACKGROUND OF THE INVENTION

The present invention relates to a new and distinct cultivar of *Hydrangea,* botanically known as *Hydrangea macrophylla* and hereinafter referred to by the name 'Robert'.

The new *Hydrangea* is a product of a planned breeding program conducted by the Inventor in Grand Haven, Mich. The objective of the breeding program was to develop new *Hydrangeas* with attractive foliage and flower coloration.

The new *Hydrangea* originated from an open-pollination in July, 2003 of the *Hydrangea macrophylla* cultivar Bailmer, disclosed in U.S. Plant Pat. No. 15,298, as the female, or seed parent and an unknown selection of *Hydrangea macrophylla.* The cultivar Robert was discovered and selected by the Inventor in May, 2005 as a flowering plant within the progeny of the stated open-pollination in a controlled environment in Grand Haven, Mich.

Asexual reproduction of the new cultivar by softwood cuttings in Grand Haven, Mich. since June, 2005 has shown that the unique features of this new *Hydrangea* plant are stable and reproduced true to type in successive generations of asexual reproduction.

SUMMARY OF THE INVENTION

The cultivar Robert has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Robert'. These characteristics in combination distinguish 'Robert' as a new and distinct cultivar of *Hydrangea:*

1. Upright and mounded plant habit.
2. Strong roots and stems.
3. Strong and dark green-colored leaves.
4. Large mophead-type inflorescences with dark pink-colored flowers.

Plants of the new *Hydrangea* differ from plants of the female parent, the cultivar Bailmer, in the following characteristics:

1. Plants of the new *Hydrangea* have darker green-colored leaves than plants of the cultivar Bailmer.
2. Flowers of plants of the new *Hydrangea* have larger and thicker sepals than flowers of plants of the cultivar Bailmer.
3. Sepals of plants of the new *Hydrangea* are brighter pink in color than sepals of plants of the cultivar Bailmer.
4. With development, sepals of plants of the new *Hydrangea* turn green in color whereas with development, sepals of plants of the cultivar Bailmer turn brown in color.

Plants of the new *Hydrangea* can be compared to plants of the cultivar Sonmarie, not patented. Plants of the new *Hydrangea* differ from plants of the cultivar Sonmarie in the following characteristics:

1. Plants of the new *Hydrangea* have glossier and darker green-colored leaves than plants of the cultivar Sonmarie.
2. Plants of the new *Hydrangea* develop inflorescences on new and old wood whereas plants of the cultivar Sonmarie only develop inflorescences on old wood.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea.*

The photograph at the bottom of the sheet comprises a side perspective view of a typical flowering plant of 'Robert' grown in an outdoor nursery.

The photograph at the top of the sheet is a close-up view of a typical inflorescence of 'Robert'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Grand Haven, Mich. in ground beds in an outdoor nursery and under conditions which closely approximate commercial production conditions. Plants of the new *Hydrangea* were about three years old when the photographs and description were taken during the summer.

Botanical description: *Hydrangea macrophylla* cultivar Robert.

Parentage:

*Female, or seed, parent.*—*Hydrangea macrophylla* cultivar Bailmer, disclosed in U.S. Plant Pat. No. 15,298.

*Male, or pollen, parent.*—Unknown selection of *Hydrangea macrophylla,* not patented.

Propagation:

*Type cutting.*—By softwood cuttings.

*Time to initiate roots.*—About ten days at temperatures of about 24° C.

*Time to produce a rooted young plant.*—About 40 days at temperatures of about 24° C.

*Root description.*—Fine, fibrous.

*Rooting habit.*—Freely branching; dense.

Plant description:

*Form/growth habit.*—Perennial shrub. Upright and mounded plant habit; broadly inverted triangle. Strong lateral branches; vigorous growth habit.

*Plant height.*—About 65 cm.

*Plant diameter or area of spread.*—About 75 cm.

*Branching habit.*—When pinched, freely branching with about seven lateral branches per plant.

*Lateral branches.*—Length: About 57 cm. Diameter: About 7 mm. Internode length: About 9 cm. Texture: Smooth, glabrous. Strength: Strong. Color: 144B with speckles, 187C.

Foliage description:

*Arrangement.*—Opposite, simple.

*Length.*—About 17 cm.

*Width.*—About 10 cm.

*Shape.*—Elliptic.

*Apex.*—Acuminate.

*Base.*—Cuneate.

*Margin.*—Serrate.

*Texture, upper and lower surfaces.*—Rugose; glabrous.

*Venation pattern.*—Pinnate.

*Color.*—Developing foliage, upper surface: 137A. Developing foliage, lower surface: 137B. Fully expanded foliage, upper surface: 137A; venation, 145B. Fully expanded foliage, lower surface: 137C; venation, 145B.

*Petiole.*—Length: About 2.2 cm. Diameter: About 4 mm. Texture, upper and lower surfaces: Smooth, glabrous. Color, upper and lower surfaces: 145B.

Flower description:

*Flower type and habit.*—Single sterile and fertile flowers arranged on terminal mophead-type panicles. Flowers face upright or outward. Flowers not fragrant.

*Natural flowering season.*—Continuous flowering from July to September in Grand Haven, Mich. Plants begin flowering about six to eight weeks after pinching.

*Flower longevity, fertile flowers.*—Flowers last about two weeks on the plant; flowers not persistent.

*Flower longevity, sterile flowers.*—Flowers last about four months on the plant; flowers persistent.

*Quantity of flowers.*—Freely flowering; about 53 fertile flowers and about 200 sterile flowers per panicle.

*Panicle height.*—About 11 cm.

*Panicle diameter.*—About 18 cm.

*Flower diameter, fertile flowers.*—About 4 mm.

*Flower depth (height), fertile flowers.*—About 5 mm.

*Flower diameter, sterile flowers.*—About 5 cm.

*Flower depth (height), sterile flowers.*—About 8 cm.

*Flower buds, fertile and sterile flowers.*—Length: About 1 mm. Diameter: About 1 mm. Shape: Globular. Color: 144D.

*Petals, fertile flowers only.*—Arrangement: Four in a single whorl. Length: About 2 mm. Width: About 1 mm. Shape: Lanceolate. Apex: Acuminate. Base: Attenuate. Margin: Entire. Texture, upper and lower surfaces: Smooth, glabrous. Color: When opening and fully opened, upper surface: 74C. When opening and fully opened, lower surface: 74C.

*Sepals, fertile flowers.*—Quantity per flower: Four in a single whorl. Length: About 2 mm. Width: About 1 mm. Shape: Deltoid. Apex: Acute. Base: Truncate. Margin: Entire. Texture, upper and lower surfaces: Smooth, glabrous. Color: When opening, upper and lower surfaces: 144D. Fully opened, upper and lower surfaces: 144D.

*Sepals, sterile flowers.*—Quantity per flower: Four in a single whorl. Length: About 2.5 cm. Width: About 2.5 cm. Shape: Oblanceolate. Apex: Acute. Base: Cuneate. Margin: Entire. Texture, upper and lower surfaces: Smooth, glabrous. Color: When opening, upper and lower surfaces: 144C. Fully opened, upper surface: 66B to 66C; color becoming closer to 144B with development. Fully opened, lower surface: 66C; color becoming closer to 144C with development.

*Peduncles, fertile and sterile flowers.*—Angle: Erect to about 20° from vertical. Strength: Strong. Length: About 7.5 cm. Diameter: About 4 mm. Texture: Smooth, glabrous. Color: 144A tinted with 66B.

*Pedicels, fertile flowers.*—Angle: Erect to about 10° from vertical. Strength: Strong. Length: About 5 mm. Diameter: About 1.5 mm. Texture: Smooth, glabrous. Color: 66B.

*Pedicels, sterile flowers.*—Angle: About 10° to about 90° from vertical. Strength: Strong. Length: About 2 cm to 2.5 cm. Diameter: About 1.5 mm. Texture: Smooth, glabrous. Color: 66B.

*Reproductive organs, fertile flowers only.*—Stamens: Quantity per flower: About five. Anther shape: Oblong. Anther length: About 1.5 mm. Anther color: 66C. Pollen amount: Moderate. Pollen color: Close to 198C. Pistils: Pistil quantity per flower: About two or three. Pistil length: About 2 mm. Stigma shape: Bi-lobed. Stigma color: 66D. Style length: About 2 mm. Style color: 66D. Ovary color: 63D.

*Seeds.*—Quantity per inflorescence: Numerous. Size: Less than 0.1 mm by less than 0.1 mm. Color: Close to 200D.

Disease/pest resistance: Plants of the new *Hydrangea* have not been observed to be resistant to pests or pathogens common to *Hydrangea.*

Temperature tolerance: Plants of the new *Hydrangea* have been shown to be tolerant to temperatures ranging from about −27° C. about 37° C.

It is claimed:

1. A new and distinct *Hydrangea* plant named 'Robert' as illustrated and described.

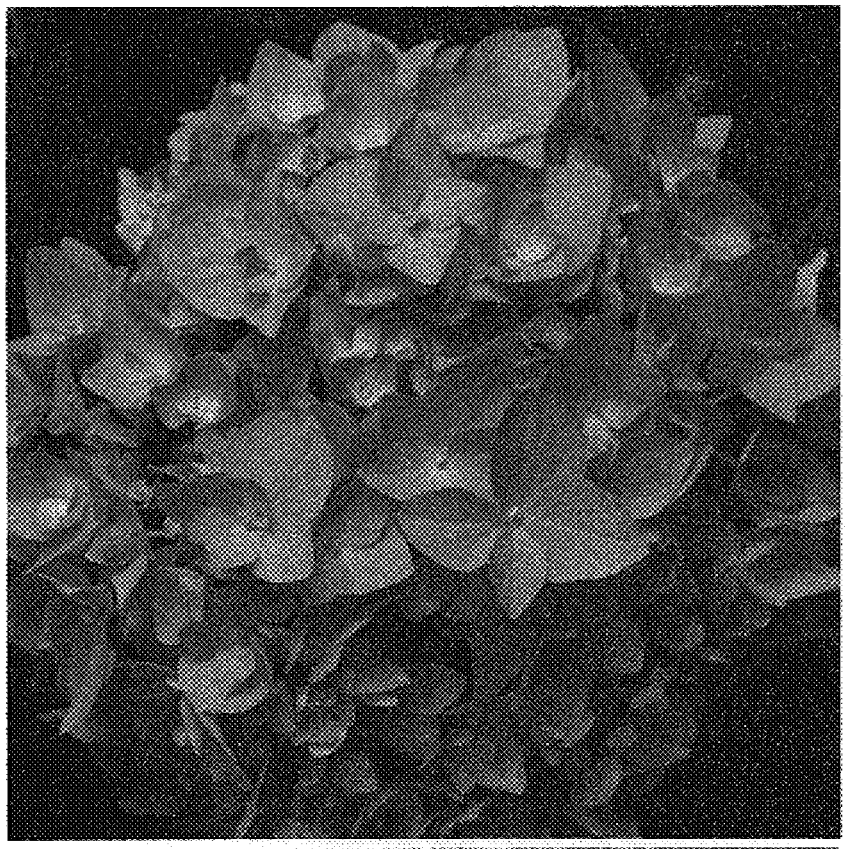
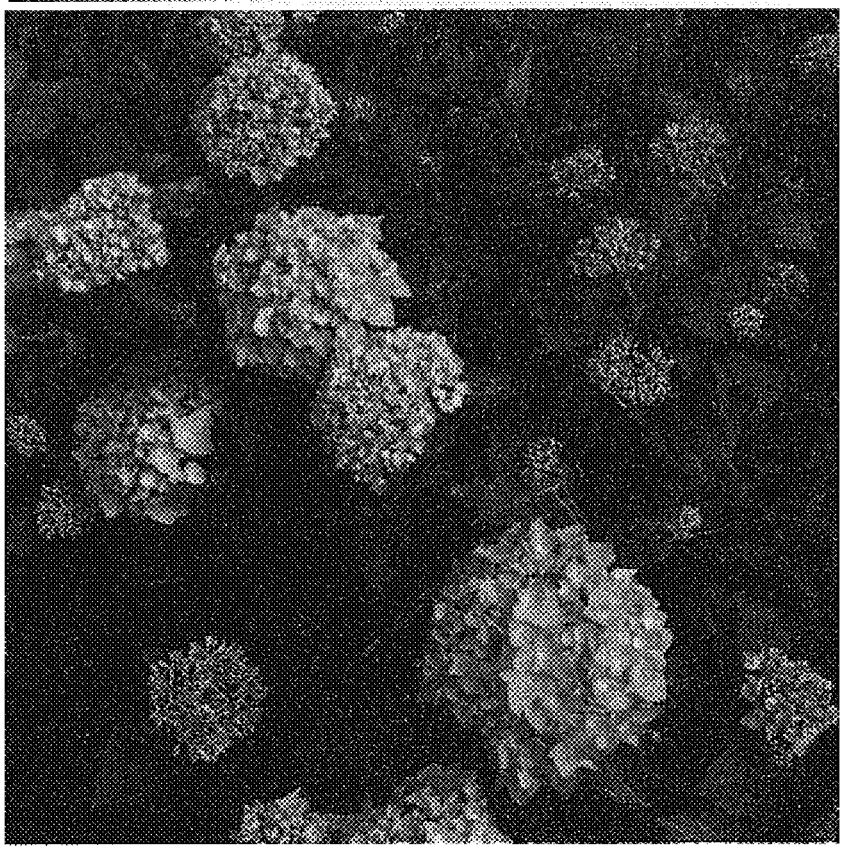

* * * * *